United States Patent [19]

Tobler et al.

[11] Patent Number: 4,460,400
[45] Date of Patent: Jul. 17, 1984

[54] DIHYDROPYRONES, NOVEL STARTING PRODUCTS USED THEREIN, COMPOSITIONS CONTAINING THE NOVEL DIHYDROPYRONES AS ACTIVE INGREDIENTS, AND THE USE THEREOF FOR COMBATING WEEDS

[75] Inventors: Hans Tobler, Allschwil; Werner Föry, Basel, both of Switzerland

[73] Assignee: Ciba-Geigy Corporation, Ardsley, N.Y.

[21] Appl. No.: 381,599

[22] Filed: May 24, 1982

[30] Foreign Application Priority Data

Jun. 3, 1981 [CH] Switzerland .............. 3630/81

[51] Int. Cl.³ .................. A01N 43/16; C07D 309/32
[52] U.S. Cl. ........................... 71/88; 549/396; 549/402; 549/420; 560/9; 560/11; 560/12; 560/13; 560/18; 560/21; 560/43; 560/45; 260/465 D
[58] Field of Search .............. 71/88; 549/396, 402, 549/420

[56] References Cited

U.S. PATENT DOCUMENTS 4,297,367  10/1981  Guigues et al. .............. 549/420
4,316,737   2/1982  Guigues et al. .............. 549/420

FOREIGN PATENT DOCUMENTS 2016463  9/1979  United Kingdom .............. 549/420

*Primary Examiner*—Nicky Chan
*Attorney, Agent, or Firm*—Frederick H. Rabin

[57] ABSTRACT

There are described novel dihydropyrones of the formula I

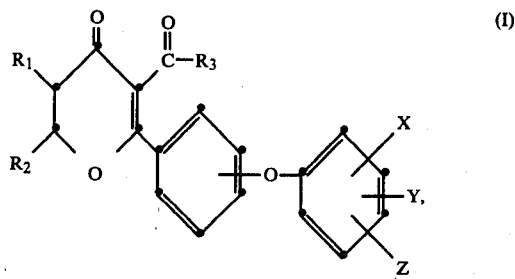

wherein $R_1$ and $R_2$ independently of one another are each a $C_1$-$C_4$-alkyl group, or one of the two substituents is also hydrogen, or $R_1$ and $R_2$ jointly form a $C_2$-$C_6$-alkylene bridge, $R_3$ is $C_1$-$C_4$-alkoxy, $C_2$-$C_6$-alkenyloxy, $C_2$-$C_4$-alkynyloxy, $C_1$-$C_4$-haloalkoxy, $C_3$-$C_5$-alkoxyalkoxy or hydroxyl, and X, Y and Z independently of one another are each hydrogen, halogen, $C_1$-$C_4$-alkyl, $C_1$-$C_4$-alkyl, $C_1$-$C_4$-alkoxy, $C_1$-$C_4$-haloalkyl, $C_1$-$C_4$-haloalkoxy, —S(O)$_n$-$C_1$-$C_4$-alkyl, —S(O)$_n$-$C_1$-$C_4$-haloalkyl, where n is 0, 1 or 2, or they are each C(O)OR$_4$, where $R_4$ is hydrogen or $C_1$-$C_4$-alkyl, or they are each NO$_2$, CN or NR$_5$R$_6$, where $R_5$ and $R_6$ independently of one another are each hydrogen, $C_1$-$C_4$-alkyl, $C_1$-$C_4$-alkylcarbonyl, $C_1$-$C_4$-haloalkylcarbonyl or $C_1$-$C_4$-haloalkylsulfonyl, processes for producing them, novel starting products used therein, and the use of the novel dihydropyrones. The active substances of the formula I can be used in the form of agriculturally applicable compositions for combating weeds.

16 Claims, No Drawings

DIHYDROPYRONES, NOVEL STARTING PRODUCTS USED THEREIN, COMPOSITIONS CONTAINING THE NOVEL DIHYDROPYRONES AS ACTIVE INGREDIENTS, AND THE USE THEREOF FOR COMBATING WEEDS

The present invention relates to novel dihydropyrones having herbicidal activity, to processes for producing them, to novel starting products used therein, to compositions containing the novel dihydropyrones as active ingredients, and to the use thereof for combating weeds.

The novel dihydropyrones, including the acid addition salts thereof, correspond to the formula I

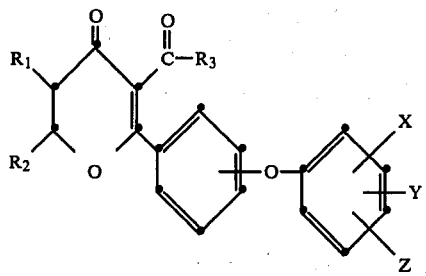

wherein $R_1$ and $R_2$ independently of one another are each a $C_1$-$C_4$-alkyl group, or one of the two substituents is also hydrogen, or $R_1$ and $R_2$ jointly form a $C_2$-$C_6$-alkylene bridge, $R_3$ is $C_1$-$C_4$-alkoxy, $C_2$-$C_6$-alkenyloxy, $C_2$-$C_4$-alkynyloxy, $C_1$-$C_4$-haloalkoxy, $C_3$-$C_5$-alkoxyalkoxy or hydroxyl, and X, Y and Z independently of one another are each hydrogen, halogen, $C_1$-$C_4$-alkyl, $C_1$-$C_4$-alkoxy, $C_1$-$C_4$-haloalkyl, $C_1$-$C_4$-haloalkoxy, -S(O)$_n$-$C_1$-$C_4$-alkyl, -S(O)$_n$-$C_1$-$C_4$-haloalkyl, where n is 0, 1 or 2, or they are each C(O)OR$_4$, where R$_4$ is hydrogen or $C_1$-$C_4$-alkyl, or they are each NO$_2$, CN or NR$_5$R$_6$, where R$_5$ and R$_6$ independently of one another are each hydrogen, $C_1$-$C_4$-alkyl, $C_1$-$C_4$-alkylcarbonyl, $C_1$-$C_4$-haloalkylcarbonyl or $C_1$-$C_4$-haloalkylsulfonyl.

$C_1$-$C_4$-Alkyl as substituent or as part of a substituent is n-propyl, isopropyl, n-butyl, sec-butyl, tert-butyl, isobutyl and in particular methyl and ethyl.

$C_2$-$C_6$-Alkenyl and $C_2$-$C_4$-alkynyl can be straight-chain or branched chain. Preferred groups are allyl and propargyl.

An alkylene bridge formed by $R_1$ and $R_2$ can be a straight-chain or branched-chain group, particularly a —(CH$_2$)$_3$— or —(CH$_2$)$_4$—group.

By halogen as substituent or as part of a substituent are meant fluorine, chlorine, bromine and iodine atoms. Haloalkyl groups can be mono- or polysubstituted by the aforementioned halogen atoms, for example CH$_2$J, CCl$_3$, CHCl$_2$, CH$_2$Br and especially CF$_3$, CHF$_2$, CH$_2$CH$_2$Cl, CF$_2$CHF$_2$, CH$_2$CF$_3$ and CH$_2$CCl$_3$.

Suitable salts are in particular metal salts, and salts with quaternary ammonium bases or organic nitrogen bases. Metals suitable for salt formation are for example: alkaline-earth metals, such as magnesium or calcium, especially however the alkali metals, such as lithium, potassium or sodium. Also applicable as salt formers are transition metals, such as iron, nickel, cobalt, copper, zinc, chromium or manganese.

Examples of quaternary ammonium bases are the ammonium cation, tetraalkylammonium cations in which the alkyl groups independently of one another are straight-chain or branched-chain $C_1$-$C_6$-alkyl groups, such as the tetramethylammonium cation, the tetraethylammonium cation or the trimethylethylammonium cation, and also the trimethylbenzylammonium cation, the triethylbenzylammonium cation, the trimethyl-2-hydroxyethylammonium cation and the trimethyl-2-chloroethylammonium cation.

Example of organic nitrogen bases suitable for forming salts are: primary, secondary and tertiary, aliphatic and aromatic amines which can be hydroxylated on the hydrocarbon radical, such as: methylamine, ethylamine, propylamine, isopropylamine, the four isomeric butylamines, dimethylamine, diethylamine, di-n-propylamine, di-isopropylamine, di-n-butylamine, pyrrolidine, piperidine, morpholine, trimethylamine, triethylamine, tri-n-propylamine, quinuclidine, pyridine, quinoline, isoquinoline as well as methanolamine, ethanolamine, propanolamine, dimethanolamine, diethanolamine or triethanolamine.

Compounds of the formula I in which $R_1$ and $R_2$ are alkyl groups can be in the form of two diastereroisomers, of which the one exhibits a cis configuration, the other a trans configuration. It is possible to separate the isomers from isomeric mixtures of compounds of the formula I in a manner known per se, for example by column chromatography. The present invention embraces cis isomers, trans isomers and isomeric mixtures of compounds of the formula I.

Preferred compounds of the formula I are those in which the phenoxy group is in the p- or m-position, especially in the p-position, and in which $R_1$ is $C_1$-$C_4$-alkyl, and $R_2$ is methyl or ethyl, or one of the substituents $R_1$ and $R_2$ is also hydrogen, or $R_1$ and $R_2$ together form a —(CH$_2$)$_3$— or —(CH$_2$)$_4$— group, $R_3$ is $C_1$-$C_4$-alkoxy, which can be straight-chain or branched-chain, or allyloxy, propargyloxy, 2,2,2-trichloroethoxy, 2,2,2-trifluoroethoxy, 2-chloroethoxy, methoxymethoxy or 2-(methoxy)-ethoxy, and one of the substituents X, Y and Z is hydrogen, and the two other substituents independently of one another are hydrogen, chlorine, bromine, iodine, fluorine, methyl, ethyl, methoxy, trifluoromethyl, trifluoromethoxy, difluoromethoxy, 1,1,2,2-tetrafluoroethoxy, methylthio, methylsulfinyl, methylsulfonyl, trifluoromethylthio, difluoromethylthio, trifluoromethylsulfinyl, methoxycarbonyl, ethoxycarbonyl, nitro, cyano, amino, methylamino or dimethylamino.

Particularly preferred compounds of the formula I are those in which the phenoxy group is in the p-position, and in which one of the substituents $R_1$ and $R_2$ is hydrogen and the other is methyl or ethyl, or $R_1$ and $R_2$ are both methyl, $R_3$ is a methoxy or ethoxy group, and one of the substituents X, Y and Z is hydrogen, and the two other substituents independently of one another are hydrogen, chlorine, methyl, trifluoromethyl, trifluoromethoxy, difluoromethylthio or cyano.

Outstanding compounds of the formula I are those in which the phenoxy group is in the p-position, $R_1$ is ethyl, $R_2$ is hydrogen, $R_3$ is a methoxy or ethoxy group, X is trifluoromethyl or trifluoromethoxy, and Y and Z are each hydrogen.

Especially preferred compounds are:
2-(4'-phenoxyphenyl)-3-methoxycarbonyl-5-methyl-5,6-dihydro-4-pyrone,
2-(4'-phenoxyphenyl)-3-methoxycarbonyl-6-methyl-5,6dihydro-4-pyrone,
2-(4'-phenoxyphenyl)-3-methoxycarbonyl-5,6-dimethyl-5,6-dihydro-4-pyrone (cis-trans mixture), 2-(4'-[4''-chlorophenoxy]-phenyl)-3-ethoxycarbonyl-5-ethyl-5,6-dihydro-4-pyrone,
2-(4'-[4''-chlorophenoxy]-phenyl)-3-ethoxycarbonyl-5,6-dimethyl-5,6-dihydro-4-pyrone (trans),
2-(4'-[4''-chlorophenoxy]-phenyl)-3-ethoxycarbonyl-5,6-dimethyl-5,6-dihydro-4-pyrone (cis),
2-(4'-[4''-chlorophenoxy]-phenyl)-3-ethoxycarbonyl-6-methyl-5,6-dihydro-4-pyrone,
2-(4'-[2'',4''-dichlorophenoxy]-phenyl)-3-ethoxycarbonyl-5-methyl-5,6-dihydro-4-pyrone,
2-(4'-[2'',4''-dichlorophenoxy]-phenyl)-3-ethoxycarbonyl-5,6-dimethyl-5,6-dihydro-4-pyrone (trans),
2-(4'-[2'',4''-dichlorophenoxy]-phenyl)-3-ethoxycarbonyl-5,6-dimethyl-5,6-dihydro-4-pyrone (cis),
2-(4'-[2''', 4''-dichlorophenoxy]-phenyl)-3-ethoxycarbonyl-5-ethyl-5,6-dihydro-4-pyrone,
2-(4''-[2'',4''-dichlorophenoxy]-phenyl)-3-ethoxycarbonyl-6-ethyl-5,6-dihydro-4-pyrone,
2-(4'-[3'''-trifluoromethyl-phenoxy]-phenyl)-3-methoxycarbonyl-5,6-dimethyl-5,6-dihydro-4-pyrone (cis-trans mixture),
2-(4'-[3''-trifluoromethyl-phenoxy]-phenyl)-3-methoxycarbonyl-5-ethyl-5,6-dihydro-4-pyrone,
2-(4'-[3''-trifluoromethyl-phenoxy]-phenyl)-3-methoxycarbonyl-5-methyl-5,6-dihydro-4-pyrone,
2-(4'-[4''-trifluoromethyl-phenoxy]-phenyl)-3-methoxycarbonyl-5,6-dimethyl-5,6-dihydro-4-pyrone (trans),
2-(4'-[4''-trifluoromethyl-phenoxy]-phenyl)-3-methoxycarbonyl-5,6-dimethyl-5,6-dihydro-4-pyrone (cis),
2-(4'-[2''-chloro-4''-trifluoromethyl-phenoxy]-phenyl)-3-methoxycarbonyl-5-ethyl-5,6-dihydro-4-pyrone,
2-(4'-[2''-chloro-4''-trifluoromethyl-phenoxy]-phenyl)-3-methoxycarbonyl-6-ethyl-5,6-dihydro-4-pyrone,
2-(4'-[2''-chloro-4''-triflurormethyl-phenoxy]-phenyl)-3-methoxycarbonyl-5-methyl-5,6-dihydro-4-pyrone,
2-(4'-[2''-chloro-4''-trifluoromethyl-phenoxy]-phenyl)-3-methoxycarbonyl-5,6-dimethyl-5,6-dihydro-4-pyrone (trans),
2-(4'-chloro-4''-trifluoromethyl-phenoxy]-phenyl)-3-methoxycarbonyl-5,6-dimethyl-5,6-dihydro-4-pyrone (cis),
2-(4'-[2''-chloro-4''-trifluoromethyl-phenoxy]-phenyl)-3-ethoxycarbonyl-5,6-dimethyl-5,6-dihydro-4-pyrone (trans),
2-(4'-[2''-chloro-4''-trifluoromethyl-phenoxy]-phenyl)-3-ethoxycarbonyl-5,6-dimethyl-5,6-dihydro-4-pyrone (cis),
2-(4'-[2''-chloro-4''-trifluoromethyl-phenoxy]-phenyl)-3-ethoxycarbonyl-6-methyl-5,6-dihydro-4-pyrone,
2-(4'-[2''-chloro-4''-trifluoromethyl-phenoxy]-phenyl)-3-ethoxycarbonyl-6-ethyl-5,6-dihydro-4-pyrone,
2-(4'-[2''-chloro-4''-trifluoromethyl-phenoxy]-phenyl)-3-ethoxycarbonyl-5-ethyl-5,6-dihydro-4-pyrone,
2-(4'-[3''-chlorophenoxy]-phenyl)-3-methoxycarbonyl-5-ethyl-5,6-dihydro-4-pyrone,
2-(4'-[3''-chlorophenoxy]-phenyl)-3-methoxycarbonyl-5,6-dimethyl-5,6-dihydro-4-pyrone (cis-trans mixture),
2-(4'-[3''-trifluoromethyl-phenoxy]-phenyl)-3-ethoxycarbonyl-5-ethyl-5,6-dihydro-4-pyrone,
2-(4'-[3'',5''-di-{trifluoromethyl}-phenoxy]-phenyl)-3-methoxycarbonyl-5-ethyl-5,6-dihydro-4-pyrone,
2-(4'-[3'',5''-dichlorophenoxy]-phenyl)-3-methoxycarbonyl-5-ethyl-5,6-dihydro-4-pyrone,
2-(4'-[3'',5''-dichlorophenoxy]-phenyl)-3-methyoxycarbonyl-5,6-dimethyl-5,6-dihydro-4-pyrone (cis-trans mixture),
2-(4'-[3'',5''-di-{trifluoromethyl}-phenoxy]-phenyl)-3-methoxycarbonyl-5,6-dimethyl-5,6-dihydro-4-pyrone (cis-trans mixture),
2-(4'-[3''-chlorophenoxy]-phenyl)-3-methoxycarbonyl-6-ethyl-5,6-dihydro-4-pyrone,
2-(4'-[3'',5''-dichlorophenoxy]-phenyl)-3-methoxycarbonyl-6-ethyl-5,6-dihydro-4-pyrone,
2-(4'-[3'',5''-di-{trifluoromethyl}-phenoxy]-phenyl)-3-methoxycarbonyl-6-ethyl-5,6-dihydro-4-pyrone,
2-(4'-[3''-trifluoromethyl-phenoxy]-phenyl)-3-methoxycarbonyl-6-ethyl-5,6-dihydro-4-pyrone,
2-(4'-[3''-trifluoromethyl-phenoxy]-phenyl)-3-methoxycarbonyl-5-isopropyl-5,6-dihydro-4-pyrone, and
2-(3'-[3''-chlorophenoxy]-phenyl)-3-methoxycarbonyl-5-ethyl-5,6-dihydro-4-pyrone.

Compounds of the formula I are produced, using a process analogous to that described in Bull. Soc. Chim. de France (1968), 288–298, by (a) reacting a compound of the formula II

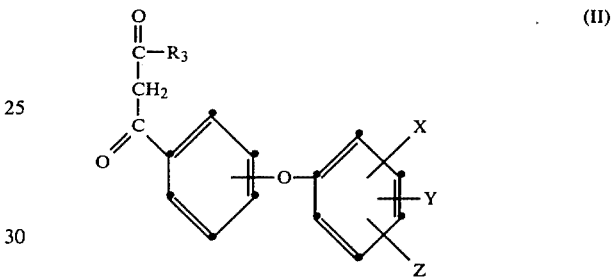

wherein $R_3$ is $C_1$-$C_4$-alkoxy, $C_2$-$C_6$-alkenyloxy, $C_2$-$C_4$-alkynyloxy, $C_1$-$C_4$-haloalkoxy or $C_3$-$C_5$-alkoxyalkoxy, and X, Y and Z independently of one another are each hydrogen, halogen, $C_1$-$C_4$-alkyl, $C_1$-$C_4$-alkoxy, $C_1$-$C_4$-haloalkyl, $C_1$-$C_4$-haloalkoxy, -S(O)$_n$-$C_1$-$C_4$-alkyl, -S(O)$_n$-$C_1$-$C_4$-haloalkyl, where n is 0, 1 or 2, or they are each C(O)OR$_4$, where R$_4$ is hydrogen or $C_1$-$C_4$-alkyl, or they are each NO$_2$, CN or NR$_5$R$_6$, where R$_5$ and R$_6$ independently of one another are each hydrogen, $C_1$-$C_4$-alkyl, $C_1$-$C_4$-alkylcarbonyl, $C_1$-$C_4$-haloalkylcarbonyl or $C_1$-$C_4$-haloalkylsulfonyl, in an inert solvent, with a compound of the formula III

Mg(OR')$_2$                           (III)

wherein R' is a straight-chain or branched-chain $C_1$-$C_4$-alkyl group;

(b) reacting the resulting reaction product, in an inert solvent, with a compound of the formula V

wherein $R_1$ and $R_2$ independently of one another are each a $C_1$-$C_4$-alkyl group, or one of the two substituents is also hydrogen, or $R_1$ and $R_2$ jointly form a $C_2$-$C_6$-alkylene bridge; and (c) cyclising the resulting product with an alcoholic solution of a strong acid, and, when $R_3$ in the formula I is hydroxyl, saponifying the ester obtained, or optionally converting in the resulting ester of the formula I the group $R_3$, by transesterification, into another group $R_3$ defined under the formula I.

The reactions described under (a) and (b) are in each case performed in an inert solvent. Suitable inert solvents are for example: benzene, toluene, xylene, ether, tetrahydrofuran or dixoane.

The reaction of a compound of the formula II with a compound of the formula III is advantageously performed at a temperature within the range of 0° to 150° C.; and the reaction of the reaction product obtained under (a) with a compound of the formula V at a temperature within the range of −10° C. to room temperature.

The magnesium alcoholate of the formula III used in the reaction described under (a) can be produced in situ by reaction of magnesium with a corresponding alcohol in the presence of $CCl_4$.

The cyclisation described under (c) can be performed with an alcoholic solution of a catalytic amount of a strong acid under reflux, for example with an alcoholic solution of hydrochloric acid, which is also obtainable in situ by reaction of acetyl chloride with alcohol.

The conversion of a group $R_3$ into another group $R_3$ defined under the formula I by transesterification can be carried out, in a manner known per se, by adding to a compound of the formula I a corresponding alcohol in the presence of a strong acid.

The production of compounds of the formula I is further illustrated by the following Examples.

PRODUCTION EXAMPLES FOR ACTIVE SUBSTANCES

Example 1

2-(4′-[3″-Chlorophenoxy]-phenyl)-3-methoxycarbonyl-5-ethyl-5,6-dihydro-4-pyrone.

(a) 10 ml of abs. methanol and 1 ml of $CCl_4$ are dissolved in 50 ml of abs. ether, and to the solution are added 1.1 g of magnesium chips. As evolution of $H_2$ commences, 13.7 g of 4-(3′-chlorophenoxy)-benzoylacetic acid methyl ester, dissolved in a small amount of ether, are added dropwise. The reaction to 2-[4′-(3″-chlorophenoxy)-benzoyl]-2-(methoxymagnesium)-acetic acid methyl ester occurs immediately with a considerable heat of reaction. To the golden-yellow solution obtained are added 100 ml of abs, toluene, and the ether as well as unreacted methanol are subsequently distilled off.

(b) The solution of 2-[4′-(3″-chlorophenoxy)-benzoyl]-2-(methoxymagnesium)-acetic acid methyl ester in toluene, obtained according to (a), is cooled to 5° C., and 5.5 g of 2-ethylacrylic acid chloride are subsequently added dropwise. The mixture is allowed to react fully for two hours at room temperature, and 50 ml of abs. acetonitrile are then added. The homogeneous solution obtained is poured into ice/conc. $H_2SO_4$ and stirred for 15 minutes. The product is extracted with ether, washed successively with 2N $H_2SO_4$, a saturated $NaHCO_3$ solution and a saturated NaCl solution, dried, and concentrated by evaporation to leave a viscous reddish-brown oil.

(c) The viscous oil obtained according to (b) is dissolved in 200 ml of methanol; there is then added 1 ml of acetyl chloride, and the solution is refluxed overnight. It is subsequently concentrated by evaporation; and the residue is taken up in ether, and treated with active charcoal. Concentration by evaporation is again performed, and the viscous oil obtained is caused to crystallise in a petroleum ether/ether mixture. The yield is 7.4 g (42.5% of theory) of 2-(4′-[3″-chlorophenoxy]-phenyl)-3-methoxycarbonyl-5-ethyl-5,6-dihydro-4-pyrone, m.p. 99°–101° C.

Example 2

2-(4′-[4″-Chlorophenoxy]-phenyl)-3-ethoxycarbonyl-5,6-dimethyl-5,6-dihydro-4-pyrone.

(a) In a manner analogous to that described in Example 1, there is prepared, from 14 g of 4-(4′-chlorophenoxy)-benzoylacetic acid ethyl ester, 1.2 g of magnesium chips and 10 ml of ethanol, a solution of 2-[4′-(4″-chlorophenoxy)-benzoyl]-2-(ethoxymagnesium)-acetic acid ethyl ester in toluene.

(b) To the solution of 2-[4′-(4″-chlorophenoxy)-benzoyl]-2-(ethoxymagnesium)-acetic acid ethyl ester in toluene obtained according to (a) are added dropwise, with cooling of the solution to −5° C., 5.7 g of 2,3-dimethylacrylic acid chloride. The mixture is allowed to fully react for 2 hours at room temperature, and 50 ml of abs. acetonitrile are added. The homogeneous solution obtained is poured into ice/conc. $H_2SO_4$ and stirred for 15 minutes. The reaction product is extracted with ether, and successively washed with 2N $H_2SO_4$, with a saturated $NaHCO_3$ solution and with a saturated NaCl solution; it is subsequently dried, and concentrated by evaporation to leave a viscous oil.

(c) The viscous oil obtained according to (b) is cyclised under reflux overnight in 200 ml of ethanol and 1 ml of acetyl chloride. The solution is concentrated by evaporation and chromatographed on 1100 g of silica gel in ether/hexane 1:1. There are isolated 4.8 g of trans-2-(4′-[4″-chlorophenoxy]-phenyl)-3-ethoxycarbonyl-5,6-dimethyl-5,6-dihydro-4-pyrone (m.p. 94°–96° C., Rf (ether/hexane 1:1) about 0.3), and also 1.2 g of cis-2-(4′-[4″-chlorophenoxy]-phenyl)-3-ethoxycarbonyl-5,6-dimethyl-5,6-dihydro-4-pyrone (m.p. 88°–90° C., Rf (ether/hexane 1:1) about 0.2). The structure was defined on the basis of the different coupling constants $J_{CH(5)-CH(6)}$ in the NMR spectrum.

[$J_{CH(5)-CH(6)}$(cis):3 Hz; $J_{CH(5)-CH(6)}$(trans):12 Hz].

The following compunds of the formula I can be produced in an analogous manner:

Table 1: Compounds of the formula

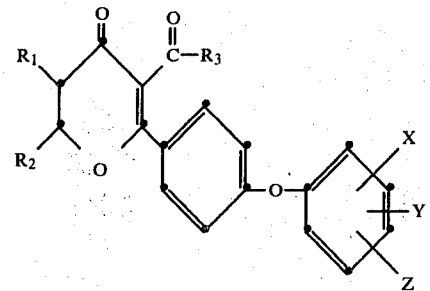

c/t = cis-/trans-isomeric mixture
c = cis isomer
t = trans isomer

TABLE 1

| No | $R_1$ | $R_2$ | $R_3$ | X | Y | Z | m.p. °C. (Constitution) | Configuration |
|----|-------|-------|-------|---|---|---|------------------------|---------------|
| 1  | $CH_3$ | H | $OCH_3$ | H | H | H | (viscous) | — |

TABLE 1-continued

| No | R₁ | R₂ | R₃ | X | Y | Z | m.p. °C. (Constitution) | Configuration |
|---|---|---|---|---|---|---|---|---|
| 2 | H | CH₃ | OCH₃ | H | H | H | 86–90 | — |
| 3 | CH₃ | CH₃ | OCH₃ | H | H | H | (viscous) | c/t |
| 4 | C₂H₅ | H | OC₂H₅ | H | 4-Cl | H | 101–102 | — |
| 5 | CH₃ | CH₃ | OC₂H₅ | H | 4-Cl | H | 94–96 | t |
| 6 | CH₃ | CH₃ | OC₂H₅ | H | 4-Cl | H | 88–90 | c |
| 7 | H | CH₃ | OC₂H₅ | H | 4-Cl | H | 96–97 | — |
| 8 | CH₃ | H | OC₂H₅ | 2-Cl | 4-Cl | H | 92–95 | — |
| 9 | CH₃ | CH₃ | OC₂H₅ | 2-Cl | 4-Cl | H | 94–97 | t |
| 10 | CH₃ | CH₃ | OC₂H₅ | 2-Cl | 4-Cl | H | 92–95 | c |
| 11 | C₂H₅ | H | OC₂H₅ | 2-Cl | 4-Cl | H | 103–104 | — |
| 12 | H | C₂H₅ | OC₂H₅ | 2-Cl | 4-Cl | H | 95–98 | — |
| 13 | CH₃ | CH₃ | OCH₃ | 3-CF₃ | H | H | 115–130 | c/t |
| 14 | C₂H₅ | H | OCH₃ | 3-CF₃ | H | H | 77–78 | — |
| 15 | CH₃ | H | OCH₃ | 3-CF₃ | H | H | 82–83 | — |
| 16 | CH₃ | CH₃ | OCH₃ | H | 4-CF₃ | H | 88–91 | t |
| 17 | CH₃ | CH₃ | OCH₃ | H | 4-CF₃ | H | (wax-like) | c |
| 18 | C₂H₅ | H | OCH₃ | 2-Cl | 4-CF₃ | H | (viscous) | — |
| 19 | H | C₂H₅ | OCH₃ | 2-Cl | 4-CF₃ | H | (viscous) | — |
| 20 | CH₃ | H | OCH₃ | 2-Cl | 4-CF₃ | H | (viscous) | — |
| 21 | CH₃ | CH₃ | OCH₃ | 2-Cl | 4-CF₃ | H | (viscous) | t |
| 22 | CH₃ | CH₃ | OCH₃ | 2-Cl | 4-CF₃ | H | (viscous) | c |
| 23 | CH₃ | CH₃ | OC₂H₅ | 2-Cl | 4-CF₃ | H | (viscous) | t |
| 24 | CH₃ | CH₃ | OC₂H₅ | 2-Cl | 4-CF₃ | H | (viscous) | c |
| 25 | H | CH₃ | OC₂H₅ | 2-Cl | 4-CF₃ | H | (viscous) | — |
| 26 | H | C₂H₅ | OC₂H₅ | 2-Cl | 4-CF₃ | H | (viscous) | — |
| 27 | C₂H₅ | H | OC₂H₅ | 2-Cl | 4-CF₃ | H | (viscous) | — |
| 28 | C₂H₅ | H | OCH₃ | 3-Cl | H | H | 98–101 | — |
| 29 | CH₃ | CH₃ | OCH₃ | 3-Cl | H | H | 123–128 | c/t |
| 30 | C₂H₅ | H | OC₂H₅ | 3-CF₃ | H | H | 63–65/80–81 | — |
| 31 | C₂H₅ | H | OCH₃ | 3-CF₃ | H | 5-CF₃ | 107–109 | — |
| 32 | C₂H₅ | H | OCH₃ | 3-Cl | H | 5-Cl | 95–97 | — |
| 33 | CH₃ | CH₃ | OCH₃ | 3-Cl | H | 5-Cl | 110–117 | c/t |
| 34 | CH₃ | CH₃ | OCH₃ | 3-CF₃ | H | 5-CF₃ | 133–135 | c/t |
| 35 | H | C₂H₅ | OCH₃ | 3-Cl | H | H | 74–76 | — |
| 36 | H | C₂H₅ | OCH₃ | 3-Cl | H | 5-Cl | 135–138 | — |
| 37 | H | C₂H₅ | OCH₃ | 3-CF₃ | H | 5-CF₃ | 112–115 | — |
| 38 | H | C₂H₅ | OCH₃ | 3-CF₃ | H | H | 87–89 | — |
| 39 | C₃H₇iso | H | OCH₃ | 3-CF₃ | H | H | 74–75 | — |
| 40 | C₂H₅ | H | OC₃H₇iso | 3-CF₃ | H | H | — | — |
| 41 | C₂H₅ | H | OC₄H₉tert | 3-CF₃ | H | H | — | — |
| 42 | C₂H₅ | H | OCH₂CH₂Cl | 3-CF₃ | H | H | — | — |
| 43 | C₂H₅ | H | OCH₂CH=CH₂ | 3-CF₃ | H | H | — | — |
| 44 | C₂H₅ | H | OCH₂C≡CH | 3-CF₃ | H | H | — | — |
| 45 | C₂H₅ | H | OCH₂CH₂OCH₃ | 3-CF₃ | H | H | — | — |
| 46 | —(CH₂)₃— | | OCH₂CF₃ | 3-CF₃ | H | H | — | — |
| 47 | —(CH₂)₄— | | OC₂H₅ | 3-CF₃ | H | H | 107–111 | c/t |
| 48 | C₃H₇iso | H | OC₂H₅ | 3-CF₃ | H | H | — | — |
| 49 | C₄H₉tert | H | OC₂H₅ | 3-CF₃ | H | H | — | — |
| 50 | C₂H₅ | H | OC₂H₅ | 3-Cl | H | H | 78–80 | — |
| 51 | C₂H₅ | H | OCH₂CCl₃ | 3-Cl | H | H | — | — |
| 52 | —(CH₂)₃— | | OC₂H₅ | 3-Cl | H | H | — | — |
| 53 | C₂H₅ | H | OC₂H₅ | 3-F | H | H | 79–80 | — |
| 54 | H | C₂H₅ | OC₂H₅ | 3-F | H | H | — | — |
| 55 | C₄H₉tert | H | OC₂H₅ | 3-F | H | H | — | — |
| 56 | C₂H₅ | H | OC₂H₅ | 3-Br | H | H | 84–85 | — |
| 57 | H | C₂H₅ | OCH₂CH=CH₂ | 3-Br | H | H | — | — |
| 58 | —(CH₂)₄— | | OC₂H₅ | 3-Br | H | H | 133–139 | c/t |
| 59 | C₂H₅ | H | OC₂H₅ | 3-J | H | H | 93–96 | — |
| 60 | H | C₂H₅ | OC₂H₅ | 3-J | H | H | — | t |
| 61 | C₂H₅ | H | OC₂H₅ | 3-OCF₃ | H | H | 54–56 | — |
| 62 | H | C₂H₅ | OC₂H₅ | 3-OCF₃ | H | H | (viscous) | — |
| 63 | C₄H₉tert | H | OC₂H₅ | 3-OCF₃ | H | H | — | — |
| 64 | C₃H₇iso | H | OC₂H₅ | 3-OCF₃ | H | H | — | — |
| 65 | C₂H₅ | H | OCH₂CH₂Cl | 3-OCF₃ | H | H | — | — |
| 66 | C₂H₅ | H | OC₂H₅ | 3-OCHF₂ | H | H | (viscous) | — |
| 67 | H | C₂H₅ | OC₂H₅ | 3-OCHF₂ | H | H | — | — |
| 68 | C₂H₅ | H | OCH₂OCH₃ | 3-OCHF₂ | H | H | — | — |
| 69 | CH₃ | CH₃ | OC₃H₇iso | 3-OCHF₂ | H | H | — | — |
| 70 | —(CH₂)₃— | | OCH₂C≡CH | 3-OCHF₂ | H | H | — | — |
| 71 | C₂H₅ | H | OC₂H₅ | 3-SCH₃ | H | H | 59–61 | — |
| 72 | H | C₂H₅ | OC₂H₅ | 3-SCH₃ | H | H | — | — |
| 73 | C₂H₅ | H | OC₃H₇n | 3-SCH₃ | H | H | — | — |
| 74 | C₂H₅ | H | OC₂H₅ | 3-SOCH₃ | H | H | — | — |
| 75 | H | C₂H₅ | OC₂H₅ | 3-SOCH₃ | H | H | — | — |
| 76 | C₂H₅ | H | OC₂H₅ | 3-SO₂CH₃ | H | H | (viscous) | — |
| 77 | C₃H₇iso | H | OC₂H₅ | 3-SO₂CH₃ | H | H | — | — |
| 78 | C₂H₅ | H | OC₂H₅ | 3-OCF₂CHF₂ | H | H | (viscous) | — |
| 79 | H | C₂H₅ | OC₂H₅ | 3-OCF₂CHF₂ | H | H | — | — |
| 80 | C₃H₇iso | H | OC₂H₅ | 3-OCF₂CHF₂ | H | H | — | — |
| 81 | C₂H₅ | H | OCH₂CH₂Cl | 3-OCF₂CHF₂ | H | H | — | — |

TABLE 1-continued

| No | $R_1$ | $R_2$ | $R_3$ | X | Y | Z | m.p. °C. (Constitution) | Configuration |
|---|---|---|---|---|---|---|---|---|
| 82 | $C_2H_5$ | H | $OC_2H_5$ | 3-$SCHF_2$ | H | H | (viscous) | — |
| 83 | —$(CH_2)_4$— | | $OC_2H_5$ | 3-$SCHF_2$ | H | H | — | — |
| 84 | $C_2H_5$ | H | $OC_2H_5$ | 3-$CH_3$ | H | H | 69–70 | — |
| 85 | H | $C_2H_5$ | $OC_2H_5$ | 3-$CH_3$ | H | H | — | — |
| 86 | $C_2H_5$ | H | $OC_2H_5$ | 3-$OCH_3$ | H | H | 64–65 | — |
| 87 | $C_2H_5$ | H | $OCH_2CCl_3$ | 3-$OCH_3$ | H | H | — | — |
| 88 | H | $C_2H_5$ | $OC_2H_5$ | 3-$OCH_3$ | H | H | — | — |
| 89 | $C_2H_5$ | H | $OCH_3$ | 3-$C(O)OCH_3$ | H | H | — | — |
| 90 | H | $C_2H_5$ | $OC_2H_5$ | 3-$C(O)OC_2H_5$ | H | H | — | — |
| 91 | $C_2H_5$ | H | $OC_2H_5$ | 3-$NO_2$ | H | H | — | — |
| 92 | $CH_3$ | $CH_3$ | $OC_2H_5$ | 3-$NO_2$ | H | H | — | — |
| 93 | $C_2H_5$ | H | $OC_2H_5$ | 3-$NH_2$ | H | H | — | — |
| 94 | $C_2H_5$ | H | $OC_2H_5$ | 3-$N(CH_3)_2$ | H | H | 78–79 | — |
| 95 | $C_2H_5$ | H | $OC_2H_5$ | 3-CN | H | H | 75–77 | — |
| 96 | H | $C_2H_5$ | $OCH_2CH_2Cl$ | 3-CN | H | H | — | — |
| 97 | $C_2H_5$ | H | $OC_2H_5$ | 3-$NHCH_3$ | H | H | — | — |
| 98 | $C_2H_5$ | H | $OC_2H_5$ | H | 4-$SCF_3$ | H | — | — |
| 99 | $C_2H_5$ | H | $OC_2H_5$ | H | 4-$SOCF_3$ | H | — | — |
| 100 | $C_2H_5$ | H | $OC_2H_5$ | H | 4-$OCHF_2$ | H | — | — |
| 101 | H | $C_2H_5$ | $OC_2H_5$ | H | 4-$OCF_3$ | H | — | — |
| 102 | H | $C_2H_5$ | $OC_2H_5$ | H | 4-F | H | — | — |
| 103 | $C_2H_5$ | H | $OC_2H_5$ | H | 4-F | H | — | — |
| 104 | $C_2H_5$ | H | $OC_2H_5$ | H | 4-J | H | — | — |
| 105 | $C_2H_5$ | H | $OC_2H_5$ | 2-F | H | H | — | — |
| 106 | $C_2H_5$ | H | $OC_2H_5$ | 2-Cl | H | H | — | — |
| 107 | H | $C_2H_5$ | $OC_2H_5$ | 2-Cl | H | H | — | — |
| 108 | $C_2H_5$ | H | $OC_2H_5$ | 2-Cl | 3-Cl | H | — | — |
| 109 | $C_2H_5$ | H | $OC_2H_5$ | 3-Cl | 4-Cl | H | — | — |
| 110 | $C_2H_5$ | H | $OC_2H_5$ | 2-Cl | H | 6-Cl | — | — |
| 111 | $C_2H_5$ | H | $OC_2H_5$ | 2-$CF_3$ | H | H | — | — |
| 112 | $C_4H_9tert$ | H | $OC_2H_5$ | 2-$CF_3$ | H | H | — | — |
| 113 | $C_2H_5$ | H | $OC_2H_5$ | H | 4-CN | H | — | — |
| 114 | H | $C_2H_5$ | $OC_2H_5$ | H | 4-CN | H | — | — |
| 115 | $C_2H_5$ | H | $OC_2H_5$ | 2-Br | H | H | — | — |
| 116 | $C_2H_5$ | H | $OC_2H_5$ | 2-Br | 3-Br | H | — | — |
| 117 | H | $C_2H_5$ | $OC_2H_5$ | 2-$OCH_3$ | H | H | — | — |
| 118 | $C_2H_5$ | H | $OC_2H_5$ | H | 4-$OCH_3$ | H | — | — |
| 119 | $C_2H_5$ | H | $OC_2H_5$ | H | 4-$SCH_3$ | H | — | — |
| 120 | H | $C_2H_5$ | $OC_2H_5$ | H | 4-$CH_3$ | H | — | — |
| 121 | $C_2H_5$ | H | $OC_2H_5$ | 3-$C_2H_5$ | H | H | — | — |
| 122 | $C_2H_5$ | H | $OC_2H_5$ | H | 4-$C_2H_5$ | H | — | — |
| 123 | $C_3H_7n$ | H | $OCH_3$ | 3-$CF_3$ | H | H | — | — |
| 124 | $C_4H_9sek$ | H | $OCH_3$ | 3-$CF_3$ | H | H | — | — |
| 125 | $C_4H_9n$ | H | $OC_2H_5$ | 3-$CF_3$ | H | H | 85–87 | — |
| 126 | $C_2H_5$ | H | $OC_2H_5$ | H | H | H | 86–88 | — |
| 127 | $CH_3$ | H | $OC_2H_5$ | 3-$CF_3$ | H | H | 96–97 | — |
| 128 | H | $C_2H_5$ | $OC_2H_5$ | 3-$CF_3$ | H | H | 70–72 | — |
| 129 | H | $C_2H_5$ | $OC_2H_5$ | 3-Br | H | H | 68–70 | — |
| 130 | $CH_3$ | $CH_3$ | $OC_2H_5$ | 3-$CF_3$ | H | H | 103–108 | c/t |
| 131 | $CH_3$ | $CH_3$ | $OC_2H_5$ | 3-Br | H | H | 129–134 | c/t |
| 132 | $CH_3$ | $CH_3$ | $OC_2H_5$ | 3-$OCF_3$ | H | H | 70–80 | c/t |
| 133 | $C_2H_5$ | H | $OC_3H_7n$ | 3-$CF_3$ | H | H | 64–67 | — |
| 134 | $C_2H_5$ | H | $OC_4H_9n$ | 3-$CF_3$ | H | H | 47–49 | — |
| 135 | $C_4H_9iso$ | H | $OC_2H_5$ | 3-Br | H | H | 74–75 | — |
| 136 | $C_4H_9iso$ | H | $OC_2H_5$ | 3-$CF_3$ | H | H | 82–83 | — |
| 137 | $C_4H_9iso$ | H | $OC_2H_5$ | 3-$OCF_3$ | H | H | 47–49 | — |
| 138 | $C_4H_9n$ | H | $OC_2H_5$ | 3-Br | H | H | 76–78 | — |
| 139 | $C_2H_5$ | H | OH | 3-$CF_3$ | H | H | (viscous) | — |
| 140 | $C_4H_9n$ | H | $OC_2H_5$ | 3-$OCF_3$ | H | H | 81–82 | — |
| 141 | —$(CH_2)_4$— | | $OC_2H_5$ | 3-$OCF_3$ | H | H | 82–86 | c/t |
| 142 | —$(CH_2)_3$— | | $OC_2H_5$ | 3-$CF_3$ | H | H | 111–112 | c |
| 143 | —$(CH_2)_3$— | | $OC_2H_5$ | 3-$OCF_3$ | H | H | 81–83 | c |
| 144 | —$(CH_2)_3$— | | $OC_2H_5$ | 3-Br | H | H | 110–111 | c |
| 145 | —$(CH_2)_4$— | | $OC_2H_5$ | 3-$OCF_3$ | H | H | 92–93 | c |

TABLE 2

[Structure diagram showing compound with R₁, R₂, R₃, X, Y, Z substituents on a phenoxy-phenyl system with carbonyl groups]

| No. | R₁ | R₂ | R₃ | X | Y | Z | Constitution | Configuration |
|-----|-----|-----|------|------|---|---|--------------|---------------|
| 146 | $C_2H_5$ | H | $OCH_3$ | 3-Cl | H | H | viscous | — |

Some of the starting products of the formula II are known (Group A), some are novel (Group B) and can be produced by processes known per se or in an analogous manner.

Group A consists of compounds of the formula II in which the phenoxy group is in the p-position, $R_3$ is $C_1$-$C_4$-alkoxy, and two of the substituents X, Y and Z are hydrogen, and the third substituent is hydrogen, fluorine, chlorine, bromine or trifluoromethyl.

Group B consists of compounds of the formula II in which $R_3$ is $C_1$-$C_4$-alkoxy, $C_2$-$C_6$-alkenyloxy, $C_2$-$C_4$-alkynyloxy, $C_1$-$C_4$-haloalkoxy or $C_3$-$C_5$-alkoxyalkoxy, and X, Y and Z independently of one another are each hydrogen, halogen, $C_1$-$C_4$-alkyl, $C_1$-$C_4$-alkoxy, $C_1$-$C_4$-haloalkyl, $C_1$-$C_4$-haloalkoxy, -S(O)$_n$-$C_1$-$C_4$-alkyl, -S(O)$_n$-$C_1$-$C_4$-haloalkyl, where n is 0, 1 or 2, or they are each C(O)OR$_4$, where R$_4$ is hydrogen or $C_1$-$C_4$-alkyl, or they are each $NO_2$, CN or NR$_5$R$_6$, where R$_5$ and R$_6$ independently of one another are each hydrogen, $C_1$-$C_4$-alkyl, $C_1$-$C_4$-alkylcarbonyl, $C_1$-$C_4$-haloalkylcarbonyl or $C_1$-$C_4$-haloalkylsulfonyl, with the proviso that, when the phenoxy group is in the p-position, $R_3$ is $C_1$-$C_4$-alkoxy, and two of the substituents X, Y and Z are hydrogen, the third substituent is not hydrogen, fluorine, chlorine, bromine or trifluoromethyl.

The compounds of the formula II, Group B, which have been specially developed for the production of the compounds of the formula I according to the invention, are still novel and likewise form subject matter of the present invention.

A process for producing 4-(4'-chlorophenoxy)-benzoyl-acetic acid ethyl ester by reaction of 4-(4'-chlorophenoxy)-benzoic acid with thionyl chloride and sodium-acetyl-acetic acid ethyl ester and subsequent deacetylation is described in Arzneimittelforschung (Pharmacological Research) 30 (1), No. 3 (1980), 454–459.

In the German Offenlegungsschrift No. 2,436,012 are described 4-phenoxy-benzoylacetic acid and alkyl esters thereof in which the phenoxy group is unsubstituted or substituted by a fluorine, chlorine or bromine atom or by a trifluoromethyl group. The alkyl esters are obtainable by Friedel-Crafts acylation of the corresponding diphenyl ethers with malonic ester chlorides, and the corresponding acids by subsequent saponification.

In addition to being obtainable by the processes already mentioned in the foregoing, compounds of the formula II can also be produced, using a process analogous to that described in J. Amer. Chem. Soc. 70 (1948), 3356–3360, by reaction of phenoxyphenyl derivatives with malonic acid methyl ester chloride.

Furthermore, compounds of the formula II in which $R_3$ is $C_1$-$C_4$-alkoxy can be produced, using a process analogous to that described in Tetrahedron 20 (1964), 1625–1632, according to the following reaction scheme:

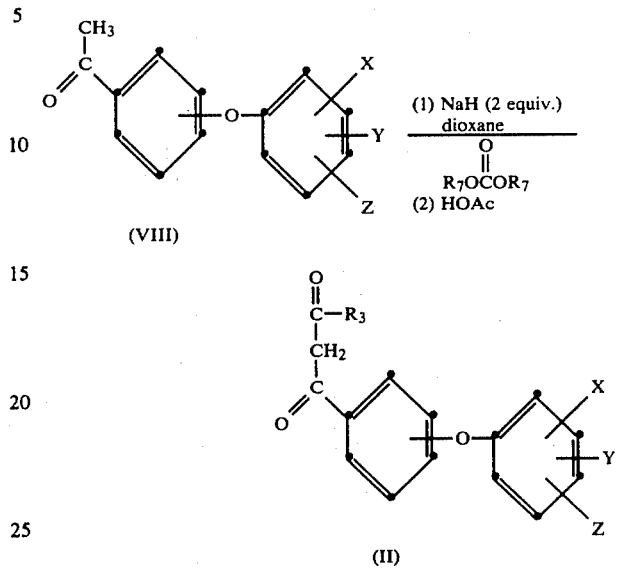

In the above formulae, X, Y and Z have the meanings given for formula II, and $R_7$ is $C_1$-$C_4$-alkyl.

The compounds of the formula VIII are known and can be produced by methods analogous to known methods (cf. for example U.S. Patent Specification No. 4,125,729; and Belgian Patent Specification No. 639,727 [Ref. in Chem. Abst. 62 (1965), 14581h]).

The production of compounds of the formula II by a process analogous to the last-mentioned process is further illustrated in the following Example.

PRODUCTION EXAMPLE FOR STARTING MATERIALS

Example 3

4-(3'-Trifluoromethyl-phenoxy)-benzoylacetic acid methyl ester.

To a mixture of 29 g of NaH (2 equiv.; 55% oil dispersion, washed three times with toluene) and 54 g of dimethylcarbonate in 400 ml of dioxane are added dropwise, at 85° C., 84.2 g of 4-(3'-trifluoromethylphenoxy)-acetonphenone dissolved in 160 ml of dioxane, whereupon an evolution of hydrogen immediately occurs. After the reaction has subsided, the reaction mixture is stirred at 85° C. for a further 2 hours, and 100 ml of acetic acid are then added dropwise with ice cooling. To the paste obtained are added 400 ml of ether and about 200 g of neutral Alox I (aluminium oxide (alumina) Woelm, activity stage I), and the mixture is filtered. The filtrate is concentrated by evaporation, dissolved in acetone, washed successively with water, a saturated NaHCO$_3$ solution and a saturated NaCL solution, dried, and concentrated by evaporation. The viscous product obtained can be used directly for the production of compounds of the formula I, or it is distilled at $10^{-2}$ Torr and 160° C., or recrystallised from hexane (m.p. 50°–55° C.). The yield of pure product is about 65 g (65% of theory).

The following compounds of the formula II can be produced in an analogous manner:

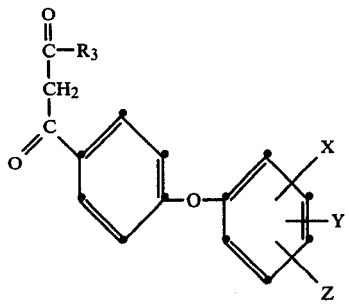

TABLE 3
Group A

| No. | R3 | X | Y | Z | m.p. °C. (Constitution) |
|---|---|---|---|---|---|
| A-1 | OCH3 | H | H | H | 48–52 |
| A-2 | OCH3 | 3-CF3 | H | H | 50–55 |
| A-3 | OCH3 | H | 4-CF3 | H | (viscous oil) |
| A-4 | OC2H5 | 3-CF3 | H | H | (viscous) |
| A-5 | OCH3 | 3-Cl | H | H | (viscous) |
| A-6 | OC2H5 | H | 4-Cl | H | — |
| A-7 | OC3H7iso | 3-CF3 | H | H | (viscous) |
| A-8 | OC4H9tert | 3-CF3 | H | H | — |
| A-9 | OC2H5 | 3-Cl | H | H | (viscous) |
| A-10 | OC2H5 | 3-F | H | H | (viscous) |
| A-11 | OC2H5 | 3-Br | H | H | (viscous) |
| A-12 | OC2H5 | H | 4-F | H | — |
| A-13 | OC2H5 | 2-F | H | H | — |
| A-14 | OC2H5 | 2-Cl | H | H | — |
| A-15 | OC2H5 | 2-CF3 | H | H | — |
| A-16 | OC2H5 | 2-Br | H | H | — |
| A-17 | OC3H7n | 3-CF3 | H | H | (viscous) |
| A-18 | OC4H9n | 3-CF3 | H | H | (viscous) |

TABLE 4
Group B

| No. | R3 | X | Y | Z | m.p. °C. (Constitution) |
|---|---|---|---|---|---|
| B-1 | OC2H5 | 2-Cl | 4-Cl | H | (viscous) |
| B-2 | OCH3 | 2-Cl | 4-CF3 | H | (viscous) |
| B-3 | OCH3 | 3-CF3 | H | 5-CF3 | 96 |
| B-4 | OCH3 | 3-Cl | H | 5-Cl | 61–63 |
| B-5 | OC2H5 | 2-Cl | 4-CF3 | H | (viscous) |
| B-6 | OCH2CH2Cl | 3-CF3 | H | H | — |
| B-7 | OCH2CH=CH2 | 3-CF3 | H | H | — |
| B-8 | OCH2C≡CH | 3-CF3 | H | H | — |
| B-9 | OCH2CH2OCH3 | 3-CF3 | H | H | — |
| B-10 | OCH2CF3 | 3-CF3 | H | H | — |
| B-11 | OCH2CCl3 | 3-Cl | H | H | — |
| B-12 | OCH2CH=CH2 | 3-Br | H | H | — |
| B-13 | OC2H5 | 3-J | H | H | (viscous) |
| B-14 | OC2H5 | 3-OCF3 | H | H | (viscous) |
| B-15 | OCH2CH2Cl | 3-OCF3 | H | H | — |
| B-16 | OC2H5 | 3-OCHF2 | H | H | (viscous) |
| B-17 | OCH2OCH3 | 3-OCHF2 | H | H | — |
| B-18 | OC3H7iso | 3-OCHF2 | H | H | — |
| B-19 | OCH2C≡CH | 3-OCHF2 | H | H | — |
| B-20 | OC2H5 | 3-SCH3 | H | H | (viscous) |
| B-21 | OC3H7n | 3-SCH3 | H | H | — |
| B-22 | OC2H5 | 3-SOCH3 | H | H | — |
| B-23 | OC2H5 | 3-SO2CH3 | H | H | (viscous) |
| B-24 | OC2H5 | 3-OCF2CHF2 | H | H | (viscous) |
| B-25 | OCH2CH2Cl | 3-OCF2CHF2 | H | H | — |
| B-26 | OC2H5 | 3-SCHF2 | H | H | (viscous) |
| B-27 | OC2H5 | 3-CH3 | H | H | (viscous) |
| B-28 | OC2H5 | 3-OCH3 | H | H | (viscous) |
| B-29 | OCH2CCl3 | 3-OCH3 | H | H | — |
| B-30 | OCH3 | 3-C(O)OCH3 | H | H | (viscous) |
| B-31 | OC2H5 | 3-C(O)OC2H5 | H | H | — |
| B-32 | OC2H5 | 3-NO2 | H | H | — |
| B-33 | OC2H5 | 3-NH2 | H | H | — |
| B-34 | OC2H5 | 3-N(CH3)2 | H | H | (viscous) |
| B-35 | OC2H5 | 3-CN | H | H | (viscous) |
| B-36 | OCH2CH2Cl | 3-CN | H | H | — |
| B-37 | OC2H5 | 3-NHCH3 | H | H | — |
| B-38 | OC2H5 | H | 4-SCF3 | H | — |
| B-39 | OC2H5 | H | 4-SOCF3 | H | — |
| B-40 | OC2H5 | H | 4-OCHF2 | H | — |
| B-41 | OC2H5 | H | 4-OCF3 | H | — |
| B-42 | OC2H5 | H | 4-J | H | — |
| B-43 | OC2H5 | 2-Cl | 3-Cl | H | — |
| B-44 | OC2H5 | 3-Cl | 4-Cl | H | — |
| B-45 | OC2H5 | 2-Cl | H | 6-Cl | — |
| B-46 | OC2H5 | H | 4-CN | H | — |
| B-47 | OC2H5 | 2-Br | 3-Br | H | — |
| B-48 | OC2H5 | 2-OCH3 | H | H | — |
| B-49 | OC2H5 | H | 4-OCH3 | H | — |
| B-50 | OC2H5 | H | 4-SCH3 | H | — |
| B-51 | OC2H5 | H | 4-CH3 | H | — |
| B-52 | OC2H5 | 3-C2H5 | H | H | — |
| B-53 | OC2H5 | H | 4-C2H5 | H | — |
| B-54 | OCH3 | 3-CN | H | H | 62–66 |

TABLE 4-continued

| | | Group B | | | |
|---|---|---|---|---|---|
| No. | R₃ | X | Y | Z | m.p. °C. (Constitution) |

[Structural formula showing a compound with R₃, CH₂, C=O groups attached to two phenyl rings connected by an O linker, with X, Y, Z substituents]

TABLE 5

| | | Group B | | | |
|---|---|---|---|---|---|
| No. | R₃ | X | Y | Z | Constitution |
| B-55 | OCH₃ | 3-Cl | H | H | viscous |

For application as herbicides, the compounds of the formula I are used either in an unmodified form or preferably together with auxiliaries customarily employed in formulation practice, and are thus processed in a known manner for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated absorptive carriers are porous types, for example pumice, ground brick, sepiolite or bentonite; and suitable nonsorbent carriers are materials such as calcite or sand. There can also be used a great number or pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$-$C_{22}$), for example the Na or K salts of oleic or stearic acid, or of natural fatty acid mixtures, which can be obtained for example from coconut oil or tallow oil. Also to be mentioned are the fatty acid-methyl-laurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbons atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:
"Mc Cutcheon's Detergents and Emulsifiers Annual", MC Publishing Corp., Ringwood, N.J., 1980, and Sisely and Wood, "Encyclopedia of Surface Active Agents", Chemical Publishing Co., Inc. N.Y., 1980.

The agrochemical preparations contain as a rule 0.1 to 99%, particularly 0.1 to 95%, of active substance of the formula I, 99.9 to 1%, of a solid or liquid additive, and 0 to 25%, in particular 0.1 to 25%, of a tenside. Whereas commercial products are preferably in the form of concentrated compositions, the compositions employed by the end-user are as a rule diluted.

The compositions can also contain further additives, such as stabilisers, antifoam agents, viscosity regulators, binders and adhesives, as well as fertilisers and other active substances for obtaining special effects.

Formulation examples for liquid active substances of the formula I (%=percent by weight)

| 4. Emulsion concentrates | (a) | (b) | (c) |
|---|---|---|---|
| active substance from Table 1 or 2 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 5. Solutions | (a) | (b) | (c) | (d) |
|---|---|---|---|---|
| active substance from Table 1 or 2 | 80% | 10% | 5% | 95% |
| ethylene glycol-monomethyl ether | 20% | — | — | — |
| polyethylene glycol M G 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very small drops.

| 6. Granulates | (a) | (b) |
|---|---|---|
| active substance from Table 1 or 2 | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| 7. Dusts | (a) | (b) |
|---|---|---|
| active substance from Table 1 or 2 | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

Formulation examples for solid active substances of the formula I (%=percent by weight)

| 8. Wettable powders | (a) | (b) | (c) |
|---|---|---|---|
| active substance from Table 1 or 2 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active substance is well mixed with the additives and the mixture is thoroughly ground in a suitable mill. Wettable powders which can be diluted with water to give suspensions of the required concentration are obtained.

| 9. Emulsion concentrate | |
|---|---|
| active substance from Table 1 or 2 | 10% |
| octylphenol polyethylene glycol ether (4–5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

| 10. Dusts | (a) | (b) |
|---|---|---|
| active substance from Table 1 or 2 | 5% | 8% |
| talcum | 95% | — |
| kaolin | — | 92% |

Dusts ready for use are obtained by mixing the active substance with the carrier and grinding the mixture in a suitable mill.

| 11. Extruder granulate | |
|---|---|
| active substance from Table 1 or 2 | 10% |
| sodium lignin sulfonate | 2% |
| carboxymethylcellulose | 1% |
| kaolin | 87% |

The active substance is mixed and ground with the additives, and the mixture is moistened with water. This mixture is extruded and then dried in a stream of air.

| 12. Coated granulate | |
|---|---|
| active substance from Table 1 or 2 | 3% |
| polyethylene glycol (M G 200) | 3% |
| kaolin | 94% |

The finely ground active substance is evenly applied, in a mixer, to the kaolin moistened with polyethylene glycol. Dustfree coated granules are obtained in this manner.

| 13. Suspension concentrate | |
|---|---|
| active substance from Table 1 or 2 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active substance is intimately mixed with the additives. There is thus obtained a suspension concentrate from which can be produced, by dilution with water, suspensions of the concentration required.

The compounds of the formula I have excellent herbicidal properties. The compounds are suitable for combating both monocotyledonous and dicotyledonous plants, and they can be applied using either the pre-emergence method or the post-emergence method. The compounds of the formula I or compositions containing them can be used particularly advantageously for selectively combating weeds in cultivated crops of cereals.

Compounds of the formula I which are particularly worthy of mention by virtue of their advantageous properties are: 2-(4'-[3''-trifluoromethyl-phenoxy]-phenyl)-3-methoxycarbonyl-5-ethyl-5,6-dihydro-4-pyrone and 2-(4'-[3''-trifluoromethy-phenoxyl]-phenyl)-3-ethoxycarbonyl-5-ethyl-5,6-dihydro-4-pyrone.

In the case of stereoisomeric compounds (for example compounds 5 and 6), the activity of the cis compound is greater than that of the trans compound.

2-Phenyl-5,6-dihydro-4-pyrones having herbicidal properties are known from the German Offenlegungsschrift No. 2,910,283. They contain on the phenyl group substituents of the group comprising halogen, $C_1$-$C_4$-alkyl and $C_1$-$C_4$-alkoxy, and these compounds are thus structually clearly different from the compounds of the formula I according to the present invention.

BIOLOGICAL EXAMPLES

Example 14 Pre-emergence herbicidal action

Immediately after sowing of the test plants in seed trays in a greenhouse, the surface of the soil was treated with an aqueous dispersion of the active substances, the dispersions having been prepared either from a 25% emulsion concentrate, or from a 25% wettable powder containing active substance which could not be prepared as an emulsion concentrate owing to inadequate solubility. A concentration of 4 kg of active substance per hectare was used. The seed trays were kept in the greenhouse at 22°-25° C. with 50-70% relative humidity, and the test results were evaluated after 3 weeks on the basis of the following scale of ratings:

1 = plants have not germinated or have completely died off,
2-3 = very intensive action,
4-6 = moderate action,
7-8 = slight action,
9 = no action (as untreated control plants)

Pre-emergence action

Amount applied: 4 kg of active substance per hectare

| Compound No. | Avena | Setaria | Sinapis | Stellaria |
|---|---|---|---|---|
| 2 | 7 | 3 | 2 | 3 |
| 5 | 7 | 4 | 5 | 3 |
| 6 | 5 | 2 | 1 | 1 |
| 7 | 7 | 5 | 4 | 1 |
| 10 | 8 | 5 | 3 | 4 |
| 13 | 7 | 2 | 2 | 1 |
| 14 | 6 | 1 | 1 | 1 |
| 15 | 6 | 2 | 3 | 1 |
| 17 | 7 | 2 | 3 | 1 |
| 19 | 7 | 4 | 4 | 2 |
| 28 | 6 | 2 | 2 | 1 |
| 29 | 9 | 4 | 2 | 1 |
| 30 | 5 | 1 | 1 | 1 |
| 35 | 7 | 1 | 1 | 1 |
| 37 | 8 | 5 | 2 | 1 |
| 38 | 6 | 1 | 1 | 1 |
| 50 | 9 | 2 | 4 | 2 |
| 56 | 6 | 1 | 1 | 1 |
| 59 | 7 | 4 | 5 | 3 |
| 61 | 7 | 1 | 1 | 1 |
| 62 | 8 | 1 | 1 | 1 |
| 66 | 6 | 3 | 1 | 2 |
| 78 | 7 | 3 | 2 | 3 |
| 82 | 9 | 1 | 5 | 1 |
| 86 | 7 | 5 | 3 | 3 |
| 127 | 6 | 1 | 1 | 2 |
| 128 | 7 | 1 | 1 | 2 |
| 129 | 7 | 3 | 1 | 3 |
| 130 | 6 | 3 | 2 | 1 |
| 132 | 6 | 1 | 1 | 1 |
| 133 | 9 | 2 | 1 | 1 |
| 134 | 8 | 5 | 3 | 1 |

Example 15 Post-emergence herbicidal action (contact herbicide)

A number of weeds, both monocotyledonous and dicotyledonous, were sprayed after emergence (in the 4- to 6-leaf stage) with an aqueous active-substance dispersion in a dosage corresponding to 4 kg of active substance per hectare, and the plants were then kept at 24°-26° C. with 45-60% relative humidity. The test was evaluated at least 15 days after the treatment, the results being assessed according to the same scale of ratings as in the pre-emergence test (Example 14).

Post-emergence action

Amount applied corresponds to 4 kg of active substance/hectare

| Comp. No. | Avena | Setaria | Lolium | Solanum | Sinapis | Stellaria | Phaseolus |
|---|---|---|---|---|---|---|---|
| 5 | 6 | 6 | 7 | 2 | 2 | 6 | 5 |
| 6 | 6 | 5 | 5 | 2 | 2 | 5 | 4 |
| 7 | 6 | 6 | 7 | 2 | 3 | 6 | 7 |
| 10 | 6 | 4 | 6 | 2 | 3 | 5 | 5 |
| 13 | 6 | 4 | 5 | 2 | 3 | 4 | 4 |

-continued

| Comp. No. | Avena | Setaria | Lolium | Solanum | Sinapis | Stellaria | Phaseolus |
|---|---|---|---|---|---|---|---|
| 14 | 6 | 4 | 4 | 1 | 3 | 4 | 3 |
| 15 | 6 | 4 | 6 | 2 | 2 | 4 | 3 |
| 17 | 6 | 4 | 5 | 2 | 3 | 4 | 4 |
| 19 | 8 | 6 | 6 | 1 | 3 | 5 | 6 |
| 26 | 8 | 6 | 6 | 2 | 3 | 4 | 6 |
| 28 | 8 | 6 | 6 | 3 | 3 | 6 | 3 |
| 29 | 8 | 6 | 6 | 3 | 3 | 6 | 6 |
| 30 | 5 | 5 | 4 | 4 | 2 | 4 | 4 |
| 33 | 7 | 9 | 9 | 4 | 4 | 5 | 6 |
| 35 | 7 | 6 | 4 | 2 | 4 | 4 | 5 |
| 37 | 8 | 7 | 9 | 3 | 4 | 6 | 6 |
| 38 | 6 | 6 | 6 | 3 | 4 | 5 | 6 |
| 50 | 6 | 4 | 5 | 3 | 3 | 3 | 3 |
| 53 | 6 | 5 | 5 | 3 | 3 | 4 | 4 |
| 56 | 8 | 7 | 6 | 2 | 2 | 4 | 5 |
| 59 | 6 | 8 | 5 | 2 | 2 | 5 | 4 |
| 61 | 6 | 3 | 4 | 2 | 3 | 4 | 4 |
| 62 | 7 | 4 | 5 | 2 | 2 | 5 | 6 |
| 66 | 6 | 6 | 3 | 2 | 2 | 5 | 3 |
| 71 | 6 | 6 | 6 | 3 | 3 | 3 | 3 |
| 76 | 7 | 6 | 6 | 3 | 3 | 3 | 4 |
| 78 | 6 | 6 | 4 | 2 | 3 | 4 | 5 |
| 82 | 7 | 7 | 6 | 3 | 3 | 3 | 4 |
| 84 | 7 | 6 | 3 | 3 | 2 | 5 | 4 |
| 86 | 6 | 6 | 3 | 2 | 2 | 4 | 3 |
| 95 | 7 | 7 | 3 | 2 | 2 | 3 | 4 |
| 127 | 6 | 6 | 6 | 3 | 4 | 6 | 5 |
| 128 | 6 | 3 | 4 | 2 | 3 | 4 | 4 |
| 129 | 7 | 3 | 4 | 2 | 3 | 4 | 5 |
| 132 | 6 | 4 | 6 | 3 | 3 | 4 | 4 |
| 133 | 6 | 6 | 6 | 4 | 3 | 5 | 5 |

What is claimed is:

1. A compound of the formula I

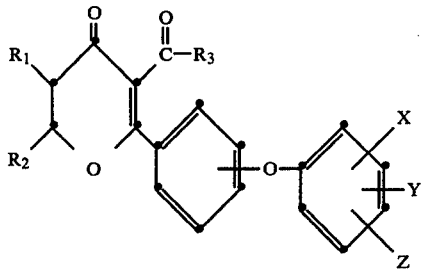

wherein $R_1$ and $R_2$ independently of one another are each a $C_1$-$C_4$-alkyl group, or one of the two substituents is also hydrogen, or $R_1$ and $R_2$ jointly form a $C_2$-$C_6$-alkylene bridge, $R_3$ is $C_1$-$C_4$-alkoxy, $C_2$-$C_6$-alkenyloxy, $C_2$-$C_4$-alkynyloxy, $C_1$-$C_4$-haloalkoxy, $C_3$-$C_5$-alkoxyalkoxy or hydroxyl, and X, Y and Z independently of one another are each hydrogen, halogen, $C_1$-$C_4$-alkyl, $C_1$-$C_4$-alkoxy, $C_1$-$C_4$-haloalkyl, $C_1$-$C_4$-haloalkoxy, -S(O)$_n$-$C_1$-$C_4$-alkyl, -S(O)$_n$-$C_1$-$C_4$-haloalkyl, where n is 0, 1 or 2, or they are each C(O)OR$_4$, where R$_4$ is hydrogen or $C_1$-$C_4$-alkyl, or they are each NO$_2$, CN or NR$_5$R$_6$, where R$_5$ and R$_6$ independently of one another are each hydrogen, $C_1$-$C_4$-alkyl, $C_1$-$C_4$-alkylcarbonyl, $C_1$-$C_4$-haloalkylcarbonyl or $C_1$-$C_4$-haloalkylsulfonyl, including the acid addition salts thereof.

2. A compound of the formula I according to claim 1, wherein the phenoxy group is in the p- or m-position, $R_1$ is $C_1$-$C_4$-alkyl and $R_2$ is methyl or ethyl, or one of the substituents $R_1$ and $R_2$ is also hydrogen, or $R_1$ and $R_2$ together form a —(CH$_2$)$_3$— or —(CH$_2$)$_4$— group, $R_3$ is $C_1$-$C_4$-alkoxy, which can be straight-chain or branched-chain, or allyloxy, propargyloxy, 2,2,2-trichloroethoxy, 2,2,2-trifluoroethoxy, 2-chloroethoxy, methoxymethoxy or 2-(methoxy)-ethoxy, and one of the substituents X, Y and Z is hydrogen, and the two other substituents independently of one another are hydrogen, chlorine, bromine, iodine, fluorine, methyl, ethyl, methoxy, trifluoromethyl, trifluoromethoxy, difluoromethoxy, 1,1,2,2-tetrafluoroethoxy, methylthio, methylsulfinyl, methylsulfonyl, trifluoromethylthio, difluoromethylthio, trifluoromethylsulfinyl, methoxycarbonyl, ethoxycarbonyl, nitro, cyano, amino, methylamino or dimethylamino.

3. A compound of the formula I according to claim 2, wherein the phenoxy group is in the p-position.

4. A compound of the formula I according to claim 3, wherein one of the substituents $R_1$ and $R_2$ is hydrogen and the other is methyl or ethyl, or $R_1$ and $R_2$ are both methyl, $R_3$ is a methoxy or ethoxy group, and one of the substituents X, Y and Z is hydrogen, and the two other substituents independently of one another are hydrogen, chlorine, methyl, trifluoromethyl, trifluoromethoxy, difluoromethylthio or cyano.

5. A compound of the formula I according to claim 4, wherein one of the substituents X, Y and Z is hydrogen, and the two other substituents independently of one another are hydrogen, chlorine, trifluoromethyl or trifluoromethoxy.

6. A compound of the formula I according to claim 5, wherein $R_1$ is ethyl, $R_2$ is hydrogen, X is trifluoromethyl or trifluoromethoxy, and Y and Z are hydrogen.

7. 2-(4'-[3''-Trifluoromethyl-phenoxy]-phenyl)-3-methoxycarbonyl-5-ethyl-5,6-dihydro-4-pyrone acording to claim 6.

8. 2-(4'-[3''-Trifluoromethyl-phenoxy]-phenyl)-3-ethoxy-carbonyl-5-ethyl-5,6-dihydro-4-pyrone according to claim 6.

9. 2-(4'-[3''-Trifluoromethoxy-phenoxy]-phenyl)-3-ethoxycarbonyl-5-ethyl-5,6-dihydro-4-pyrone according to claim 6.

10. 2-(4'-[3''-Trifluoromethoxy-phenoxy]-phenyl)-3-ethoxycarbonyl-6-ethyl-5,6-dihydro-4-pyrone according to claim 5.

11. 2-(4'-[3''-Trifluoromethyl-phenoxy]-phenyl)-3-n-propoxycarbonyl-5-ethyl-5,6-dihydro-4-pyrone according to claim 3.

12. A herbicidal composition comprising, as active ingredient, a herbicidally effective amount of a compound of the formula I according to claim 1 and a carrier.

13. A herbicidal composition according to claim 12, which contains 0.1 to 99 percent by weight of a compound of the formula I, and 1 to 99.9 percent by weight of a solid or liquid additive, including 0 to 25 percent by weight of a tenside.

14. A herbicidal composition according to claim 13, which contains 0.1 to 95 percent by weight of a compound of the formula I, 5 to 99.8 percent by weight of a solid or liquid additive, and 0.1 to 25 percent by weight of a tenside.

15. A method for combating weeds, which method comprises applying thereto a herbicidally effective amount of a compound of the formula I according to claim 1.

16. A method according to claim 15 for selectively combating weeds in cultivated crops of cereals.

* * * * *